US011969432B2

(12) United States Patent
Barnas

(10) Patent No.: US 11,969,432 B2
(45) Date of Patent: Apr. 30, 2024

(54) PHARMACEUTICAL COMPOSITION AND USE THEREOF

(71) Applicant: Usso Barnas, Innsbruck (AT)

(72) Inventor: Usso Barnas, Innsbruck (AT)

( * ) Notice: Subject to any disclaimer, the term of this patent is extended or adjusted under 35 U.S.C. 154(b) by 71 days.

(21) Appl. No.: 17/354,753

(22) Filed: Jun. 22, 2021

(65) Prior Publication Data

US 2021/0401854 A1 Dec. 30, 2021

(30) Foreign Application Priority Data

Jun. 26, 2020 (EP) .................................. 20182558

(51) Int. Cl.

| | | |
|---|---|---|
| *A61K 31/5513* | (2006.01) | |
| *A61K 9/00* | (2006.01) | |
| *A61K 31/135* | (2006.01) | |
| *A61K 31/196* | (2006.01) | |
| *A61K 31/197* | (2006.01) | |
| *A61K 31/4152* | (2006.01) | |
| *A61K 31/4415* | (2006.01) | |
| *A61K 31/455* | (2006.01) | |
| *A61K 31/525* | (2006.01) | |
| *A61K 31/542* | (2006.01) | |
| *A61K 31/573* | (2006.01) | |
| *A61K 31/714* | (2006.01) | |
| *A61P 25/04* | (2006.01) | |

(52) U.S. Cl.
CPC ........ *A61K 31/5513* (2013.01); *A61K 9/0019* (2013.01); *A61K 31/135* (2013.01); *A61K 31/196* (2013.01); *A61K 31/197* (2013.01); *A61K 31/4152* (2013.01); *A61K 31/4415* (2013.01); *A61K 31/455* (2013.01); *A61K 31/525* (2013.01); *A61K 31/542* (2013.01); *A61K 31/573* (2013.01); *A61K 31/714* (2013.01); *A61P 25/04* (2018.01)

(58) Field of Classification Search
CPC .............. A61K 31/5513; A61K 9/0019; A61K 31/135; A61K 31/196; A61K 31/197; A61K 31/4152; A61K 31/4415; A61K 31/455; A61K 31/525; A61K 31/542; A61K 31/573; A61K 31/714; A61P 25/04

USPC .......................................................... 514/52

See application file for complete search history.

(56) References Cited

FOREIGN PATENT DOCUMENTS

| | | |
|---|---|---|
| EP | 2857016 A1 | 4/2015 |
| WO | 2009/143297 A1 | 11/2009 |
| WO | 2010/039861 A2 | 4/2010 |

OTHER PUBLICATIONS

Stefancic et al. Local Administration of Morphine for Cancer Pain Management. Libri Oncol., vol. 38 (2010), No. 1-3, 65-68. (Year: 2010).*
Uzun et al. The Addition of Metamizole to Morphine and Paracetamol Improves Early Postoperative Analgesia and Patient. Turkish Neurosurgery (2010), vol. 20, No. 3, 341-347 (Year: 2010).*
European Patent Office: "Extended European Search Report"; dated Dec. 14, 2020; EESR in related EP application No. 20182558.5.
Nemec et al.: "Evidence-based intravenous pain treatement with analgesic infusion regimens"; 2010; Arzneimittelforschung; pp. 256-261.
Ahmed et al.: "PC-40 An evaluation of pharmacist prescribing for patients with hypertension"; May 16, 2007; Parm. World Sci. 31:40 141; Springer.

* cited by examiner

*Primary Examiner* — Yih-Horng Shiao
(74) *Attorney, Agent, or Firm* — Bryan W. Bockhop; Bockhop Intellectual Property Law, LLC

(57) ABSTRACT

The present invention discloses a pharmaceutical composition, wherein the pharmaceutical composition is an injectable or infusable pharmaceutical composition, the pharmaceutical composition comprising:
  a) a pharmaceutically acceptable solvent,
  b) a first compound comprising diclofenac and/or lornoxicam or a pharmaceutically acceptable salt or solvate thereof,
  c) a second compound comprising metamizole or tramadol or a pharmaceutically acceptable salt or solvate thereof, and
  d) a third compound selected as at least one benzodiazepine or a pharmaceutically acceptable salt or solvate thereof,
the pharmaceutical composition further comprising a cortisone derivative or a pharmaceutically acceptable salt or solvate thereof.

18 Claims, No Drawings

PHARMACEUTICAL COMPOSITION AND USE THEREOF

CROSS-REFERENCE TO RELATED APPLICATION(S)

This application claims the benefit of EP Patent Application No. EP20182558.5, filed Jun. 26, 2020, the entirety of which is hereby incorporated herein by reference.

BACKGROUND OF THE INVENTION

1. Field of the Invention

This invention relates to a pharmaceutical composition, in particular to an injectable or infusable pharmaceutical composition, comprising a pharmaceutically acceptable solvent, a first compound comprising diclofenac and/or lornoxicam or a pharmaceutically acceptable salt or solvate thereof, a second compound comprising metamizole or tramadol or a pharmaceutically acceptable salt or solvate thereof, and a third compound selected as at least one benzodiazepine or a pharmaceutically acceptable salt or solvate thereof, as well as its use in the treatment of pain in a mammal, in particular in a human.

2. Description of the Related Art

Pain is a perception mediated by the activation of certain brain structures. Pain is usually initiated when specialized neurons, termed nociceptors, which innervate the skin or other peripheral tissue, are activated by mechanical, thermal, chemical or other noxious stimuli. Pain is also experienced when peripheral or central neuronal structures involved in the processing of pain become hyperactive, e.g. as a result of trauma, ischemia or inflammation. Other causes of pain include disease-specific processes, metabolic disturbances, muscle spasm, and the onset of a neuropathic event or syndrome.

Pain treatment of almost any type usually includes one or more analgesic drugs which are usually classified into three groups: primary non-opioid, opioid, and co-analgesics, also known as adjuvants.

Non-opioid analgesic drugs include for example acetaminophen and nonsteroidal anti-inflammatory drugs or NSAIDs. These drugs can be effective for treating mild to moderate pain.

Opioid drugs, sometimes referred to as narcotics, include natural substances such as opium, opium-derived substances, such as morphine, and semi-synthetic and synthetic substances, such as fentanyl.

Co-analgesic medications are drugs that typically address indications other than pain relief but possess analgesic action for certain painful conditions. An example of a co-analgesic drug is gabapentin, which has a primary indication for the treatment of epilepsy, but also is effective in treating some kinds of neuropathic pain.

However, even if a wide variety of drugs are available for treating pain, in many cases it is still difficult to provide an effective treatment of pain or pain-associated syndromes to many patients, which are in need of such treatment. Especially patients with severe and/or chronic pain, have sometimes to cope with enormous restrictions in respect to their private and professional activities as well as in respect to their quality of life in general.

This in part is caused by the individual disease profile of many patients suffering from pain, which sometimes cannot be effectively treated by a single pain-alleviating drug. Many patients, i.e. many patients with severe and/or chronic pain have to participate in long-term treatment programs, wherein the effect of many different pain-alleviating drugs is examined, sometimes in a non-systematic approach, resulting very often in no improvement or only in a minor improvement of the individual disease profile of said patients suffering from pain.

Therefore, despite a wide range of available medical treatments, pain continues to afflict dozens of millions of individuals throughout the world and remains a profound burden to patients, health care, and business. New methods are required for increasing the efficacy of intervention and reducing the side effects associated with pain management in the clinical setting.

US 2001/0019725 discloses sustained-release compositions and a method of preparing pharmaceutical compositions.

US 2015/0320685 discloses methods and compositions which comprise effective amounts of analgesic to treat a subject, including reducing or eliminating an adverse effect associated with the analgesic.

U.S. Pat. No. 8,097,651 B2 discloses methods and formulations for treating migraine and other acute pain episodes using diclofenac, and formulations of diclofenac that provide both rapid and sustained relief from acute pain.

EP 1 150 660 B1 relates to a stable pharmaceutical effervescent formulation with metamizole and its pharmaceutically acceptable salts as an active ingredient.

U.S. Pat. No. 4,115,574A discloses benzodiazepine derivatives.

Nemec at al., XP055738529, discloses evidence-based intravenous pain treatment with analgesic infusion regimens.

SUMMARY OF THE INVENTION

It is an object of the present invention to provide a pharmaceutical composition, comprising a plurality of various compounds, which can used to treat pain or pain-related syndromes in patients with need thereof, in particular in patients suffering from severe and/or chronic pain.

According to a first aspect the present invention is directed to a pharmaceutical composition, wherein the pharmaceutical composition is an injectable or infusable pharmaceutical composition, the pharmaceutical composition comprising:
- a) a pharmaceutically acceptable solvent,
- b) a first compound comprising diclofenac and/or lornoxicam or a pharmaceutically acceptable salt or solvate thereof,
- c) a second compound comprising metamizole or tramadol or a pharmaceutically acceptable salt or solvate thereof, and
- d) a third compound selected as at least one benzodiazepine or a pharmaceutically acceptable salt or solvate thereof, wherein the pharmaceutical composition further comprises a cortisone derivative or a pharmaceutically acceptable salt or solvate thereof.

In particular the present invention relates to pharmaceutical compositions according to claims 1 to 11 and according to the embodiments in the description.

According to a second aspect the present invention is directed to a pharmaceutical composition for use in the preemptive or palliative treatment of pain in a mammal, preferably in an human, wherein preferably pain is selected from the group consisting of chronic pain, inflammatory pain, neuropathic pain, acute pain, surgical pain, cancer-related pain, disc prolapse-related pain, low-back pain, neck ache, back pain, rheumatic pain, tension-type pain, tension-type headache, migraine pain, radicular pain, tooth pain, joint pain, and pain of the locomotor apparatus, wherein the pharmaceutical composition is administered to the mammal, preferably human, until a visual analog scale (VAS) rating of pain of 3 or less is reached, and wherein the pharmaceutical composition is an injectable or infusable pharmaceutical composition, the pharmaceutical composition comprising:
 a) a pharmaceutically acceptable solvent,
 b) a first compound comprising diclofenac and/or lornoxicam or a pharmaceutically acceptable salt or solvate thereof,
 c) a second compound comprising metamizole or tramadol or a pharmaceutically acceptable salt or solvate thereof, and
 d) a third compound selected as at least one benzodiazepine or a pharmaceutically acceptable salt or solvate thereof.

In particular the present invention relates to pharmaceutical compositions for use in the preemptive or palliative treatment of pain in a mammal, preferably in an human according to claim 12 and according to the embodiments in the description.

According to a third aspect the present invention is directed to a method of preparing a pharmaceutical composition, comprising admixing a therapeutically effective amount of a first, second and third compound or a pharmaceutically acceptable salt or solvate thereof according to the first aspect with a pharmaceutically acceptable solvent according to the first aspect.

In particular the present invention relates to a method of preparing a pharmaceutical composition according to claim 13 and according to the embodiments in the description.

According to a fourth aspect the present invention is directed to a pharmaceutical composition obtainable by a method of preparing according to the third aspect.

Additional embodiments and advantages of the invention will be set forth in part in the description that follows.

The present invention and the scope thereof is defined by the appended claims. The more generic description of the invention is provided for illustrative purposes only. Embodiments not falling under these claims are for reference purposes only.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

DETAILED DESCRIPTION OF THE INVENTION

A preferred embodiment of the invention is now described in detail. Referring to the drawings, like numbers indicate like parts throughout the views. Unless otherwise specifically indicated in the disclosure that follows, the drawings are not necessarily drawn to scale. The present disclosure should in no way be limited to the exemplary implementations and techniques illustrated in the drawings and described below. As used in the description herein and throughout the claims, the following terms take the meanings explicitly associated herein, unless the context clearly dictates otherwise: the meaning of "a," "an," and "the" includes plural reference, the meaning of "in" includes "in" and "on."

According to a first aspect the present invention is directed to a pharmaceutical composition, wherein the pharmaceutical composition is an injectable or infusable pharmaceutical composition, the pharmaceutical composition comprising:
 a) a pharmaceutically acceptable solvent,
 b) a first compound comprising diclofenac and/or lornoxicam or a pharmaceutically acceptable salt or solvate thereof,
 c) a second compound comprising metamizole or tramadol or a pharmaceutically acceptable salt or solvate thereof, and
 d) a third compound selected as at least one benzodiazepine or a pharmaceutically acceptable salt or solvate thereof.

The pharmaceutical composition according to the first aspect is an injectable or infusable pharmaceutical composition comprising a pharmaceutically acceptable solvent, wherein said pharmaceutically acceptable solvent may comprise a single pharmaceutically acceptable solvent or plurality of different pharmaceutically acceptable solvents.

An pharmaceutically acceptable solvent according the present invention is an solvent, which can be applied to a mammal, preferably human, which is well tolerable by the mammal, preferably human, and can for example comprise water or water-comprising solutions.

By providing the solvent-based injectable or infusable pharmaceutical composition, said pharmaceutical composition can be effectively applied to the mammal, preferably human, in need thereof.

In comparison to conventional pain-alleviating tablets, by injecting or infusing the pharmaceutical composition according to the present invention into the blood stream of the patient, it can be ensured that the compounds of the pharmaceutical composition are effectively directed towards their designated target, while simultaneously a reduced concentration of the respective compounds of the pharmaceutical composition can be used, thereby mitigating any side effects of said compounds.

The pharmaceutical composition according to the first aspect comprises three compounds, a first compound, a second compound and a third compound. However, according to the scope of the present invention, the pharmaceutical composition according to the present invention can comprise additional compounds, beside the first, second and third compound.

The first compound comprises diclofenac and/or lornoxicam or a pharmaceutically acceptable salt or solvate thereof. This means that as a first alternative, the first compound exclusively comprises diclofenac or a pharmaceutically acceptable salt or solvate thereof. This means that as a second alternative the first compound exclusively comprises lornoxicam or a pharmaceutically acceptable salt or solvate thereof. This means that as a third alternative, the first compound comprises both diclofenac and lornoxicam or a pharmaceutically acceptable salt or solvate thereof.

Diclofenac is a nonsteroidal anti-inflammatory drug (NSAID) used to treat pain and inflammatory diseases and comprises the chemical formula, 2-[2-(2,6-dichloroanilino)phenyl]acetic acid. In particular, it provides an effective pain- and inflammation-alleviating effect.

Lornoxicam is a non-steroidal anti-inflammatory drug (NSAID) from the group of oxicams with analgesic, anti-inflammatory and anti-pyretic properties and comprises the chemical formula, 6-chloro-4-hydroxy-2-methyl-1,1-dioxo-N-pyridin-2-ylthieno[2,3-e]thiazine-3-carboxamide. In particular, it provides an effective pain- and inflammation-alleviating effect.

By using either diclofenac or lornoxicam as first compound according to alternatives 1 and 2 cited above, respectively, an effective pain- and inflammation-alleviating effect could be observed even if one of either diclofenac or lornoxicam could not be used to treat the patient in need thereof, for example due to drug intolerance in respect to diclofenac or lornoxicam.

By using diclofenac and lornoxicam in combination as first compound according to alternative 3 cited above, respectively, the effective pain- and inflammation-alleviating effect of both diclofenac and lornoxicam could be combined to obtain even further synergies in respect to a pain- and inflammation-alleviating effect.

The second compound comprises metamizole or tramadol or a pharmaceutically acceptable salt or solvate thereof.

This means that as a first alternative, the second compound exclusively comprises metamizole or a pharmaceutically acceptable salt or solvate thereof. This means that as a second alternative the first compound exclusively comprises tramadol or a pharmaceutically acceptable salt or solvate thereof. However, the first compound in particular cannot comprises both metamizole and tramadol or a pharmaceutically acceptable salt or solvate thereof.

Metamizole is a painkiller, spasm reliever, and fever reliever that also has anti-inflammatory effects and comprises the chemical formula [(1,5-dimethyl-3-oxo-2-phenylpyrazol-4-yl)-methylamino]methanesulfonic acid. In particular, it provides an effective pain-alleviating effect.

Tramadol is an opioid pain medication used to treat pain and comprises the chemical formula (1R,2R)-2-[(dimethylamino)methyl]-1-(3-methoxyphenyl)cyclohexan-1-ol. In particular, it provides an effective pain-alleviating effect.

By using either metamizole or tramadol as second compound according to alternatives 1 and 2 cited above, respectively, an effective pain-alleviating effect could be observed even if one of either metamizole or tramadol could not be used to treat the patient in need thereof, for example due to drug intolerance in respect to metamizole or tramadol.

The third compound comprises at least one benzodiazepine or a pharmaceutically acceptable salt or solvate thereof. This means said third compound may comprise a single benzodiazepine or a plurality of different benzodiazepines.

Benzodiazepines are a class of psychoactive drugs whose core chemical structure is the fusion of a benzene ring and a diazepine ring. Benzodiazepines enhance the effect of the neurotransmitter gamma-aminobutyric acid (GABA) at the $GABA_A$ receptor, resulting in sedative, hypnotic, anxiolytic, anticonvulsant, and muscle relaxant properties. As an example the class of benzodiazepines comprise diazepine, which comprises the chemical formula 1H-diazepine.

In particular, the benzodiazepines used as a third compound of the pharmaceutical composition according to the present invention provide an effective muscle relaxing effect, thereby further stimulating the pain-alleviating effect of the pharmaceutical composition according to the present invention.

An important finding when applying the pharmaceutical composition of the present invention to patients suffering from pain and/or pain-related syndromes, is that when applying the pharmaceutical composition, an effective alleviation of pain could be observed even within a relative short time span.

Often these patients have previously suffered from severe and/or chronic pain, which has led to an sometimes dramatic decrease of quality of life and has sometimes diminished their ability to live a normal private and professional life. Often, before applying the pharmaceutical composition according to the present invention, these patients have undergone a classic pain treatment using conventional pain killers, such as for example paracetamol, seractil or even diclofenac without any additional compounds, mostly without any significant or long-lasting effect.

However, when applying the pharmaceutical composition according to the present invention, which comprises the combination of the first, second and third compound, a significant improvement of pain and/or pain-related syndromes in these patients could be observed within a rather short time span, sometimes even within a few days or few weeks, depending on the severity of pain, the respective patient suffers from.

In particular, when applying a pain rating, for example by employing the visual analog scale (VAS), the effect can, in particular be demonstrated when comparing the pain ratings of patients, which have suffered from major pain of 8 or more, sometimes even 9 or more, for weeks or months, with the respective pain ratings after treatment with the pharmaceutical composition of the present invention, wherein pain ratings of less than 2, sometimes even less than 1, can be observed sometimes after a few days. For further details in this respect, reference is provided to the examples section of the present application.

Therefore, the superior effect of the pharmaceutical composition of the present invention compared to conventional pain killers used in the prior art is based on a synergetic, and thereby self-amplifying, effect, of the combination of the first, second and third compound, when comparing with the effect of conventionally used individual pain killers.

In particular the combination of at least two pain- and inflammation-ameliorating compounds according to the combination of the first and second compound together with at least one benzodiazepine according to the third compound, which provides an effective muscle relaxation, different metabolic pathways in the patient can be targeted by the respective compounds, thereby affecting not only a single cause of the pain, but instead a plurality of causes of pain, the patient suffers from.

As summarized above, diclofenac and/or lornoxicam according to the first compound, metamizole or tramadol according to the second compound, and/or at least one benzodiazepine according to the third compound can be selected as a pharmaceutically acceptable salt thereof.

An pharmaceutically acceptable salt according to the present invention comprises any salt of diclofenac, lornoxicam, metamizol, tramadol and/or a benzodiazepine, which can be applied to a mammal, preferably human, which is well tolerable by the mammal, preferably human.

In particular a pharmaceutically acceptable salt according to the present invention comprises all non-toxic pharmaceutically acceptable salts thereof of the disclosed compounds. Examples of pharmaceutically acceptable addition salts include inorganic and organic acid addition salts and basic salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate and the like.

Acid addition salts can be formed by mixing a solution of the particular compound of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, or the like. Basic salts can be formed by mixing a solution of the compound of the present invention with a solution of a pharmaceutically acceptable non-toxic base such as sodium hydroxide, potassium hydroxide, choline hydroxide, sodium carbonate and the like.

As summarized above, diclofenac and/or lornoxicam according to the first compound, metamizole or tramadol according to the second compound, and/or at least one benzodiazepine according to the third compound can be selected as a pharmaceutically acceptable solvate thereof.

According to the present invention, solvates typically do not significantly alter the physiological activity or toxicity of the compounds, and as such may function as pharmacological equivalents. The term "solvate" as used herein is a combination, physical association and/or solvation of a compound of the present invention with a solvent molecule such as, e.g. a disolvate, monosolvate or hemisolvate, where the ratio of solvent molecule to compound of the present invention is 2:1, 1:1 or 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates.

Diclofenac, lornoxicam, metamizol, tramadol and/or a benzodiazepine can be present as solvated forms with a pharmaceutically acceptable solvent, such as for example water, and the like, and it is intended that the invention includes both solvated and unsolvated forms of compounds of any of said compounds. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et. al, J. Pharmaceut. Sci., 93(3):601-611 (2004), which describes the preparation of solvates of fluconazole with ethyl acetate and with water. Similar preparation of solvates, hemisolvates, hydrates, and the like are described by E. C. van Tonder et al., AAPS Pharm. Sci. Tech., 5(1): Article 12 (2004), and A. L. Bingham et al., Chem. Commun.: 603-604 (2001).

The first, second and third compound of the pharmaceutical composition can be mixed together with the pharmaceutically acceptable solvent to provide a single injectable or infusable pharmaceutical composition.

According to an embodiment, the at least one benzodiazepine or pharmaceutically acceptable salt or solvate thereof comprises diazepam, delorazepam and/or chlonazepam or a pharmaceutically acceptable salt or solvate thereof.

By selecting diazepam, delorazepam and/or chlonazepam or a pharmaceutically acceptable salt or solvate an advantageous injectable or infusable pharmaceutical composition can be provided.

According to a first alternative the at least one benzodiazepine comprises only diazepam or a pharmaceutically acceptable salt or solvate thereof. According to a second alternative the at least one benzodiazepine comprises only delorazepam or a pharmaceutically acceptable salt or solvate thereof. According to a third alternative the at least one benzodiazepine comprises only chlonazepam or a pharmaceutically acceptable salt or solvate thereof. According to a fourth alternative the at least one benzodiazepine comprises any combination of diazepam, delorazepam and chlonazepam or pharmaceutically acceptable salts or solvates thereof.

According to an embodiment, the third compound comprises from 0.00001 wt.-% to 0.00004 wt.-% of the least one benzodiazepine or pharmaceutically acceptable salt or solvate thereof, preferably from 0.000016 wt.-% to 0.00003 wt.-%, more preferably from 0.000016 wt.-% to 0.000025 wt.-%, and most preferably 0.00002 wt.-%.

By selecting the preferred concentration ranges for the at least one benzodiazepine an effective muscle relaxing effect can be observed when treating patients suffering from pain, which results in an effective reduction of pain syndromes.

Throughout the present disclosure, the term wt.-% in respect to a compound refers to the weight-percentage of said compound in respect to the total weight of the pharmaceutical composition. For example, if the pharmaceutical comprises 0.00002 wt.-% of a benzodiazepine, and the total weight of the pharmaceutical composition is 250 g, then 5 mg of the benzodiazepine is present in the pharmaceutical composition.

According to an embodiment, the pharmaceutical composition comprises from 0.00012 wt.-% to 0.0012 wt.-% of diclofenac or a pharmaceutically acceptable salt or solvate thereof, preferably from 0.0002 wt.-% to 0.008 wt.-%, and most preferably 0.0003 wt.-% or 0.0006 wt.-%.

By selecting the preferred concentration ranges for diclofenac or a pharmaceutically acceptable salt or solvate thereof an effective pain-relieving and/or anti-inflammation effect can be observed when treating patients suffering from pain, which results in an effective reduction of pain-related syndromes.

According to an embodiment, the pharmaceutical composition comprises from 0.000008 wt.-% to 0.000128 wt.-% of lornoxicam or a pharmaceutically acceptable salt or solvate thereof, preferably from 0.000032 wt.-% to 0.000096 wt.-%, and most preferably 0.000032 wt.-% or 0.000064 wt.-%.

Lornoxicam or a pharmaceutically acceptable salt or solvate thereof provides an effective pain-relieving and/or anti-inflammation effect and can be used as an alternative to diclofenac, for example if diclofenac is not tolerated by a patient. Alternatively diclofenac and lornoxicam can be used in combination within the pharmaceutical composition.

According to an embodiment, the pharmaceutical composition further comprises paracetamol or a pharmaceutically acceptable salt or solvate thereof, preferably from 0.001 wt.-% to 0.008 wt.-% of paracetamol or a pharmaceutically acceptable salt or solvate thereof, more preferably from 0.0025 wt.-% to 0.008 wt.-%, and most preferably 0.004 wt.-% or 0.008 wt.-%.

By adding paracetamol, which corresponds to N-Acetyl-4-aminophenol, to the pharmaceutical composition of the present invention, in addition to the first, second and third compound, the pain-relieving effect of the pharmaceutical composition could be increased.

Preferably, paracetamol or a pharmaceutically acceptable salt or solvate can be mixed with the first, second and third compound of the pharmaceutical composition within the pharmaceutically acceptable solvent to provide a single injectable or infusable pharmaceutical composition. As an alternative, paracetamol or a pharmaceutically acceptable salt or solvate can be applied separately to the mixture of the first, second and third compound of the pharmaceutical composition with the pharmaceutically acceptable solvent to provide two separate portions of the injectable or infusable pharmaceutical composition, which are applied separately to the patient.

According to an embodiment, the pharmaceutical composition comprises from 0.002 wt.-% to 0.01 wt.-% of metamizole or a pharmaceutically acceptable salt or solvate thereof, preferably from 0.003 wt.-% to 0.007 wt.-%, and most preferably 0.005 wt.-%.

By selecting the preferred concentration ranges for metamizole or a pharmaceutically acceptable salt or solvate an effective pain-relieving effect can be observed when treating patients suffering from pain, which results in an effective reduction of pain-related syndromes.

According to an embodiment, the pharmaceutical composition comprises from 0.0002 wt.-% to 0.0008 wt.-% of tramadol or a pharmaceutically acceptable salt or solvate thereof, preferably from 0.0003 wt.-% to 0.0006 wt.-%, and most preferably 0.0004 wt.-%.

Tramadol or a pharmaceutically acceptable salt or solvate thereof provides an effective pain-relieving effect and can be used as an alternative to metamizol, for example if metamizole is not tolerated by a patient.

According to an embodiment, the pharmaceutical composition comprises diclofenac or a pharmaceutically acceptable salt or solvate thereof, metamizole or a pharmaceutically acceptable salt or solvate thereof and diazepam or a pharmaceutically acceptable salt or solvate thereof.

By selecting diclofenac or a pharmaceutically acceptable salt or solvate thereof as first compound, metamizole or a pharmaceutically acceptable salt or solvate thereof as second compound and diazepam or a pharmaceutically acceptable salt or solvate as third compound, a pharmaceutical composition can be provided to the patient with a particularly effective pain-relieving effect.

According to an embodiment, the pharmaceutical composition comprises diclofenac or a pharmaceutically acceptable salt or solvate thereof, tramadol or a pharmaceutically acceptable salt or solvate thereof and diazepam or a pharmaceutically acceptable salt or solvate thereof.

By selecting diclofenac or a pharmaceutically acceptable salt or solvate thereof as first compound, tramadol or a pharmaceutically acceptable salt or solvate thereof as second compound and diazepam or a pharmaceutically acceptable salt or solvate as third compound, a pharmaceutical composition can be provided to the patient with a particularly effective pain-relieving effect. In this respect metamizole can be replaced by tramadol as second compound, for example if metamizole is not well tolerated by the patient.

According to an embodiment, the pharmaceutical composition comprises lornoxicam or a pharmaceutically acceptable salt or solvate thereof, metamizole or a pharmaceutically acceptable salt or solvate thereof and diazepam or a pharmaceutically acceptable salt or solvate thereof.

By selecting lornoxicam or a pharmaceutically acceptable salt or solvate thereof as first compound, metamizole or a pharmaceutically acceptable salt or solvate thereof as second compound and diazepam or a pharmaceutically acceptable salt or solvate as third compound, a pharmaceutical composition can be provided to the patient with a particularly effective pain-relieving effect. In this respect diclofenac can be replaced by lornoxicam as first compound, for example if diclofenac is not well tolerated by the patient.

According to an embodiment, the pharmaceutical composition comprises lornoxicam or a pharmaceutically acceptable salt or solvate thereof, tramadol or a pharmaceutically acceptable salt or solvate thereof and diazepam or a pharmaceutically acceptable salt or solvate thereof.

By selecting lornoxicam or a pharmaceutically acceptable salt or solvate thereof as first compound, tramadol or a pharmaceutically acceptable salt or solvate thereof as second compound and diazepam or a pharmaceutically acceptable salt or solvate as third compound, a pharmaceutical composition can be provided to the patient with a particularly effective pain-relieving effect. In this respect diclofenac can be replaced by lornoxicam as first compound and metamizole can be replaced by tramadol as second compound, for example if diclofenac and metamizole is not well tolerated by the patient.

According to an embodiment, the pharmaceutical composition further comprises a vitamin B additive composition, wherein the vitamin B additive composition preferably comprises thiamine, riboflavin, nicotinamide, cobalamin, dexapanthenol and/or pyridoxin or a pharmaceutically acceptable salt or solvate thereof.

By adding the vitamin B additive composition to the pharmaceutical composition a particular increase in pain-relieving effect of the pharmaceutical composition could be observed when applying the pharmaceutical composition to patients in need thereof. Preferably the vitamin B additive composition comprises a single compound or any combination of the following compounds, thiamine, riboflavin, nicotinamide, cobalamin, dexapanthenol and/or pyridoxin or a pharmaceutically acceptable salt or solvate thereof.

According to an embodiment, the vitamin B additive composition comprises from 0.000004 wt.-% to 0.000022 wt.-% of thiamine or a pharmaceutically acceptable salt or solvate thereof, preferably from 0.00001 wt.-% to 0.000022 wt.-%, and most preferably 0.0000108 wt.-% or 0.000022 wt.-%.

According to an embodiment, the vitamin B additive composition comprises from 0.0000008 wt.-% to 0.0001 wt.-% of riboflavin or a pharmaceutically acceptable salt or solvate thereof, preferably from 0.0000012 wt.-% to 0.0000038 wt.-%, and most preferably 0.00000188 wt.-% or 0.0000038 wt.-%.

According to an embodiment, the vitamin B additive composition comprises from 0.000026 wt.-% to 0.00011 wt.-% of nicotinamide or a pharmaceutically acceptable salt or solvate thereof, preferably from 0.000036 wt.-% to 0.00011 wt.-%, and most preferably 0.000056 wt.-% or 0.00011 wt.-%.

According to an embodiment, the vitamin B additive composition comprises from 0.000002 wt.-% to 0.000008 wt.-% of dexapanthenol or a pharmaceutically acceptable salt or solvate thereof, preferably from 0.000003 wt.-% to 0.000008 wt.-%, and most preferably 0.000004 wt.-% or 0.000008 wt.-%.

According to an embodiment, the vitamin B additive composition comprises from 0.000002 wt.-% to 0.0000076 wt.-% of pyridoxin or a pharmaceutically acceptable salt or solvate thereof, preferably from 0.000002 wt.-% to 0.0000076 wt.-%, and most preferably 0.000004 wt.-% or 0.0000076 wt.-%.

According to an embodiment, the vitamin B additive composition comprises from 0.0000004 wt.-% to 0.000004 wt.-% of cobalamin or a pharmaceutically acceptable salt or solvate thereof, and most preferably 0.000002 wt.-% or 0.000004 wt.-%.

According to the first aspect, the pharmaceutical composition further comprises a cortisone derivative or a pharmaceutically acceptable salt or solvate thereof.

The cortisone derivative or a pharmaceutically acceptable salt or solvate thereof, which is added to the pharmaceutical composition allows for an anti-inflammation and anti-swelling effect. This allows for example for a pressure reduction in the area of the spinal cord, the nerve roots and/or peripheral nerves, which can be caused by inflamed and swollen connecting tissue at the spinal cord, thereby resulting in a relaxation of the spinal cord.

According to an embodiment, the cortisone derivative or pharmaceutically acceptable salt or solvate thereof comprises dexamethasone, betamethasone, methylprednisolone, prednisolone, triamcinolone acetonide or a pharmaceutically acceptable salt or solvate thereof.

The cortisone derivative or pharmaceutically acceptable salt or solvate thereof can be selected as a single compound or as any combination of the following compounds, dexamethasone, betamethasone, methylprednisolone, prednisolone, triamcinolone acetonide or a pharmaceutically acceptable salt or solvate thereof.

According to an embodiment, the pharmaceutical composition comprises from 0.000008 wt.-% to 0.00004 wt.-% of betamethasone or a pharmaceutically acceptable salt or solvate thereof, preferably from 0.00001 wt.-% to 0.00003 wt.-%, and most preferably 0.000012 wt.-% or 0.000024 wt.-%.

According to an embodiment, the pharmaceutical composition comprises from 0.00002 wt.-% to 0.00016 wt.-% of dexamethasone or a pharmaceutically acceptable salt or solvate thereof, preferably from 0.00003 wt.-% to 0.0001 wt.-%, and most preferably 0.00004 wt.-% or 0.00008 wt.-%.

According to an embodiment, the pharmaceutical composition comprises from 0.00004 wt.-% to 0.00064 wt.-% of triamcinolone acetonide or a pharmaceutically acceptable salt or solvate thereof, preferably from 0.0001 wt.-% or 0.0008 wt.-%, and most preferably 0.00024 wt.-% or 0.0004 wt.-%.

According to an embodiment, the pharmaceutical composition comprises from 0.00005 wt.-% to 0.001 wt.-% of prednisolone or a pharmaceutically acceptable salt or solvate thereof, and most preferably 0.0005 wt.-% or 0.001 wt.-%.

According to an embodiment, the pharmaceutical composition comprises from 0.000008 wt.-% to 0.000256 wt.-% of methylprednisolone or a pharmaceutically acceptable salt or solvate thereof, preferably from 0.0001 wt.-% to 0.0002 wt.-%, and most preferably 0.000064 wt.-% or 0.000128 wt.-%.

According to an embodiment, the pharmaceutically acceptable solvent is selected as an aqueous solution comprising sodium chloride, calcium chloride, potassium chloride, magnesium chloride, sodium acetate and/or glucose.

An aqueous solution as pharmaceutically acceptable solvent is well tolerable by the patient, while the added salts provide electrolytes to the patient suffering from pain.

According to an embodiment, the aqueous solution is selected as an aqueous sodium chloride solution, preferably comprising from 0.1 wt.-% to 2.0 wt.-% sodium chloride, more preferably from 0.5 wt.-% to 1.5 wt.-%, even more preferably from 0.8 wt.-% to 1.2 wt.-%, and most preferably comprising 0.9 wt.-% sodium chloride.

According to an embodiment, the aqueous solution is selected as an aqueous glucose solution comprising from 0.1 wt.-% to 20 wt.-% glucose, preferably from 0.5 wt. % to 10 wt.-%, more preferably from 1 wt.-% to 10 wt.-% and most preferably 5 wt.-%.

According to an embodiment, the aqueous solution is selected as an aqueous electrolyte solution comprising sodium chloride, calcium chloride dihydrate, potassium chloride, magnesium chloride hexahydrate and/or sodium acetate trihydrate,
  (i) preferably comprising from 0.001 wt.-% to 1.0 wt.-% sodium chloride, preferably comprising 0.0055 wt.-%,
  (ii) preferably comprising from 0.0001 wt.-% to 1.0 wt.-% calcium chloride dihydrate, preferably 0.000368 wt.-%,
  (iii) preferably comprising from 0.0001 wt.-% to 1.0 wt.-% potassium chloride, preferably 0.000373 wt.-%,
  (iv) preferably comprising from 0.0001 wt.-% to 1.0 wt.-% magnesium chloride hexahydrate, preferably 0.000305 wt.-%, and/or
  (v) preferably comprising from 0.001 wt.-% to 1.0 wt.-% sodium acetate trihydrate, preferably 0.006124 wt.-%.

The above-referenced aqueous solution is also referred to as ELO-MEL isotone infusion solution.

According to an embodiment, the aqueous solution is selected as an aqueous lactate solution comprising sodium chloride, calcium chloride dihydrate, potassium chloride, and/or sodium lactate,
  (i) preferably comprising from 0.001 wt.-% to 1.0 wt.-% sodium chloride, preferably comprising 0.006 wt.-% sodium chloride,
  (ii) preferably comprising from 0.0001 wt.-% to 1.0 wt.-% calcium chloride dihydrate, preferably 0.00027 wt.-%,
  (iii) preferably comprising from 0.0001 wt.-% to 1.0 wt.-% potassium chloride, preferably 0.00040 wt.-%, and/or
  (iv) preferably comprising from 0.001 wt.-% to 1.0 wt.-% sodium lactate, preferably 0.00624 wt.-%.

The above-referenced aqueous solution is also referred to as Ringer lactate infusion solution.

The embodiments and preferred selections for the pharmaceutical composition according to the first aspect can be combined without any limitations.

According to a second aspect the present invention is directed to a pharmaceutical composition for use in the preemptive or palliative treatment of pain in a mammal, preferably in an human, wherein preferably pain is selected from the group consisting of chronic pain, inflammatory pain, neuropathic pain, acute pain, surgical pain, cancer-related pain, disc prolapse-related pain, low-back pain, neck ache, back pain, rheumatic pain, tension-type pain, tension-type headache, migraine pain, radicular pain, tooth pain, joint pain, and pain of the locomotor apparatus, the pharmaceutical composition comprising:
  a) a pharmaceutically acceptable solvent,
  b) a first compound comprising diclofenac and/or lornoxicam or a pharmaceutically acceptable salt or solvate thereof,
  c) a second compound comprising metamizole or tramadol or a pharmaceutically acceptable salt or solvate thereof, and
  d) a third compound selected as at least one benzodiazepine or a pharmaceutically acceptable salt or solvate thereof.

Thereby, the technical advantage is achieved that the pharmaceutical composition according to the present invention can be effectively used in alleviating pain and/or pain-related syndromes for a variety of different types of pain.

According to an embodiment, the pharmaceutical composition is administered to the mammal, preferably human, by injection or infusion.

By applying the pharmaceutical composition to the patient by injection or infusion a rapid effect of the compounds of the pharmaceutical composition can be typically observed. Also when applying the pharmaceutical composition to the patient by injection or infusion the concentrations of the compounds present in the pharmaceutical composition can be significantly reduced compared for example to the oral appliance of traditional pain killers.

According to an embodiment, the pharmaceutical composition is administered to the mammal, preferably human, for a period of less than 30 days, preferably less than 20 days, more preferably less than 15 days, even more preferably less than 10 days, most preferably less than 7 days and even most preferably less than 5 days to at least partially reduce the pain in the mammal, preferably human.

Therefore, an at least partial reduction of pain can be observed within a relatively short time span, which in the best case can encompass only a few days before a significant improvement of pain syndromes can be experienced by the patient.

Preferably, the duration of administration of the pharmaceutical composition can be shorter when the patient is only suffering from acute pain, while the duration of administration of the pharmaceutical composition can be longer when the patient is suffering from chronic pain.

In case the patient experiences acute pain, the pharmaceutical composition is preferably administered to the mammal, preferably human, for a period of less than 5 days to at least partially reduce the pain in the mammal, preferably human, more preferably even only for 2 or 3 days.

In case the patient experiences chronic pain, the pharmaceutical composition is preferably administered to the mammal, preferably human, for a period of less than 15 days to at least partially reduce the pain in the mammal, preferably human, more preferably even only for 7 to 14 days.

According to an embodiment, the pharmaceutical composition is administered to the mammal, preferably human, one time, one-to-two times, two times, two-to-three times, three times, three-to-four times, or four times a day, wherein preferably the time interval between the respective administrations is at least 2 hours, more preferably at least 3 hours and most preferably at least 4 hours.

Therefore, an individual dosing procedure can be applied to each individual patient, depending on the severity of the pain and/or pain-related syndromes.

According to the second aspect, the pharmaceutical composition is administered to the mammal, preferably human, until a visual analog scale (VAS) rating of pain of 3 or less is reached, preferably of 2 or less and most preferably of 1 or less.

Therefore, when a visual analog scale (VAS) rating of pain of 3 or less, or even lower, is reached, it can be concluded that the severity of pain and/or pain-related syndromes has been at least partially improved.

The visual analog scale (VAS) can be determined according to Escalona-Marfil C., et al., Validation of an Electronic Visual Analog Scale mHealth Tool for Acute Pain Assessment: Prospective Cross-Sectional Study, J Med Internet Res. 2020, 22(2), e13468.

Typically the visual analog scale (VAS) rating of pain encompasses numerical values ranging from 0, wherein the patient does not experience any pain, to 10, wherein the patient suffers from the worst possible pain.

Even if the intensity of pain is considered to be experienced by the individual patient on a subjective base, it has to be emphasized that by comparing visual analog scale (VAS) ratings of pain of a plurality of patients after experiencing different pain treatments, trends in respect to the effectivity of the treatment can be recognized, in particular when significant differences can be derived from said pain treatments.

According to an embodiment, the pharmaceutical composition is applied at room temperature.

According to an embodiment, the pharmaceutical composition is applied at a rate from 3 ml/min to 10 ml/min, preferably between 5 ml/min and 6 ml/min.

According to an embodiment, the volume of the applied pharmaceutical composition is between 100 ml and 300 ml, preferably 250 ml.

The embodiments and preferred selections for the pharmaceutical composition for use according to the second aspect can be combined without any limitations.

The embodiments and preferred selections for the pharmaceutical composition according to the first aspect are also embodiments and preferred selections for the pharmaceutical composition for use according to the second aspect.

According to a third aspect the present invention is directed to a method of preparing a pharmaceutical composition, comprising admixing a therapeutically effective amount of a first, second and third compound or a pharmaceutically acceptable salt or solvate thereof according to the first aspect with a pharmaceutically acceptable solvent according to the first aspect.

Therefore, an effective and easy-to-perform preparation of the respective pharmaceutical composition can be performed by the medical practitioner shortly before applying the respective pharmaceutical composition to the patient in need thereof, or alternatively the respective pharmaceutical composition can be prepared in advance by a pharmacist and then stored safely before applying the respective pharmaceutical composition to the patient in need thereof.

In particular, the first, second and/or third compound of the respective pharmaceutical composition are provided in solvatized, e.g. liquid, form, so that in this case the solvatized first, second and/or third compound can be directly poured into the pharmaceutically acceptable solvent without any risk of precipitation occurring.

According to an embodiment, the method of preparing a pharmaceutical composition, comprises adding a therapeutically effective amount of a vitamin B additive composition according to an embodiment of the first aspect.

According to an embodiment, the method of preparing a pharmaceutical composition, comprises adding a therapeutically effective amount of a cortisone derivative or a pharmaceutically acceptable salt or solvate thereof according to an embodiment of the first aspect.

In particular, the vitamin B additive composition and/or the cortisone derivative of the respective pharmaceutical composition are provided in solvatized, e.g. liquid, form, so that in this case the solvatized vitamin B additive composition and/or the solvatized cortisone derivative can be directly poured into the pharmaceutically acceptable solvent without any risk of precipitation occurring.

The embodiments and preferred selections for the method of preparing a pharmaceutical composition according to the third aspect can be combined without any limitations.

The embodiments and preferred selections for the pharmaceutical composition according to the first aspect and the embodiments and preferred selections for the pharmaceutical composition for use according to the second aspect, are also embodiments and preferred selections for the method of preparing a pharmaceutical composition according to the third aspect.

According to a fourth aspect the present invention is directed to a pharmaceutical composition obtainable by a method of preparing according to the third aspect.

The embodiments and preferred selections for the pharmaceutical composition according to the first aspect, and the embodiments and preferred selections for the pharmaceutical composition for use according to the second aspect, and the embodiments and preferred selections for the method of preparing a pharmaceutical composition according to the third aspect are also embodiments and preferred selections for the pharmaceutical composition obtainable by a method of preparing according to the fourth aspect.

The embodiments and preferred selections for the pharmaceutical composition according to the first aspect, and the embodiments and preferred selections for the pharmaceutical composition for use according to the second aspect, and the embodiments and preferred selections for the method of preparing a pharmaceutical composition according to the third aspect, and the embodiments and preferred selections for the pharmaceutical composition obtainable by a method of preparing according to the fourth aspect, are also embodiments and preferred selections for the method of treating pain according to the fifth aspect.

EXAMPLES

Example Compositions

In the following example compositions 1 to 23 are summarized, which represent specific embodiments of the pharmaceutical compositions according to the present invention. The example compositions 1 to 23 can be used for the treatment of pain in a mammal, preferably in a human. For specific data in respect to the selected example compositions 1 and 14 for the treatment of pain in human patients reference to the section "pain treatment studies" below is provided.

The example compositions 1 to 23 are injectable or infusable pharmaceutical compositions, which means that example compositions 1 to 23 can be administered to a patient in need of treatment by injecting or infusing the example compositions 1 to 23 into the blood stream of the patient. Therefore, the example compositions 1 to 23 comprise a pharmaceutically acceptable solvent, in which pharmaceutically active compounds are dissolved.

In each of the example compositions 1 to 23 an aqueous sodium chloride solution, in particular comprising 0.9 wt.-% of sodium chloride, is used as an pharmaceutically acceptable solvent. The total volume of each of the example compositions 1 to 23 is 250 ml. However, it is possible to use additional or alternative pharmaceutically acceptable solvents in the same or different volumes, for example the specific pharmaceutically acceptable solvents cited in the present invention, in particular an ELO-MEL or Ringer lactate solution.

Each of the example compositions 1 to 23 comprises a first compound, a second compound and a third compound according to the subject matter of the present invention, wherein the first, second and/or third compound may comprise a pharmaceutically acceptable salt or solvate thereof. For example in example composition 1, the first compound is selected as a pharmaceutically acceptable salt of diclofenac, in particular diclofenac-sodium.

According to the present invention the first compound can comprise diclofenac and/or lornoxicam or a pharmaceutically acceptable salt or solvent thereof. This means that lornoxicam can be used as an alternative to diclofenac or that diclofenac and lornoxicam can be used in combination.

According to the present invention the first compound can comprise metamizole or tramadol or a pharmaceutically acceptable salt or solvent thereof. This means that tramadol can be used as an alternative to metamizole.

According to the present invention the third compound is selected as at least one benzodiazepine or a pharmaceutically acceptable salt or solvent thereof. This means that the third compound may comprise a single benzodiazepine or a plurality of different benzodiazepines. Benzodiazepines are a class of psychoactive drugs whose core chemical structure is the fusion of a benzene ring and a diazepine ring. In particular the benzodiazepines used in the example compositions 1 to 23 comprises diazepam, delorazepam and/or chlonazepam or a pharmaceutically acceptable salt or solvate thereof.

Although in the example compositions 1 to 23 specific amounts of the first, second and/or third compound are specified it is possible to modify the concentrations of the first, second and/or third compound according to the disclosure of the present invention.

Each of the example compositions 1 to 23 may optionally comprise a vitamin B additive composition and/or a cortisone derivative.

The components of the vitamin B additive composition may be selected according to the disclosure of the present invention and may comprise thiamine, riboflavin, nicotinamide, cobalamin, dexapanthenol and/or pyridoxin or a pharmaceutically acceptable salt or solvent thereof, in particular at the concentrations according to the disclosure of the present invention.

The cortisone derivative may be selected according to the disclosure of the present invention and may comprise dexamethasone, betamethasone, methylprednisolone, prednisolone, and/or triamcinolone acetonide or a pharmaceutically acceptable salt or solvent thereof, in particular at the concentrations according to the disclosure of the present invention.

The example compositions 1 to 23 are summarized in the following:

Example Composition 1

| Component | Volume/Amount |
|---|---|
| 0.9 wt.-% sodium chloride solution | 250 mL |
| Diclofenac-sodium | 75 mg |
| Metamizol-sodium | 1.12 g |
| Diazepam | 5 mg |
| Vitamin B additive composition (total): | 19.17 mg (total) |
| Thiamine hydrochloride | 2.7 mg |
| Sodium riboflavinephosphate | 0.47 mg |
| Nicotinamide | 14 mg |
| Dexapanthenol | 1 mg |
| Pyridoxin-Hydrochloride | 1 mg |

Example Composition 2

| Component | Volume/Amount |
|---|---|
| 0.9 wt.-% sodium chloride solution | 250 mL |
| Diclofenac-sodium | 110 mg |
| Metamizol-sodium | 1.12 g |
| Benzodiazepine | 10 mg |
| Vitamin B additive composition | 37.85 mg |

Example Composition 3

| Component | Volume/Amount |
|---|---|
| 0.9 wt.-% sodium chloride solution | 250 mL |
| Diclofenac-sodium | 75 mg |
| Tramadol hydrochloride | 100 mg |
| Benzodiazepine | 4 mg |

Example Composition 4

| Component | Volume/Amount |
|---|---|
| 0.9 wt.-% sodium chloride solution | 250 mL |
| Diclofenac-sodium | 110 mg |
| Tramadol hydrochloride | 100 mg |
| Benzodiazepine | 10 mg |

Example Composition 5

| Component | Volume/Amount |
|---|---|
| 0.9 wt.-% sodium chloride solution | 250 mL |
| Diclofenac-sodium | 75 mg |
| Metamizol-sodium | 1.12 g |
| Benzodiazepine | 4 mg |
| Vitamin B additive composition | 19.17 mg |
| Cortisone derivative | 2.6 mg |

Example Composition 6

| Component | Volume/Amount |
|---|---|
| 0.9 wt.-% sodium chloride solution | 250 mL |
| Diclofenac-sodium | 75 mg |
| Metamizol-sodium | 1.12 g |
| Benzodiazepine | 4 mg |
| Vitamin B additive composition | 19.17 mg |
| Cortisone derivative | 5.3 mg |

Example Composition 7

| Component | Volume/Amount |
|---|---|
| 0.9 wt.-% sodium chloride solution | 250 mL |
| Diclofenac-sodium | 75 mg |
| Metamizol-sodium | 1.12 g |
| Benzodiazepine | 4 mg |
| Vitamin B additive composition | 19.17 mg |
| Cortisone derivative | 10 mg |

Example Composition 8

| Component | Volume/Amount |
|---|---|
| 0.9 wt.-% sodium chloride solution | 250 mL |
| Diclofenac-sodium | 75 mg |
| Metamizol-sodium | 1.12 g |
| Benzodiazepine | 4 mg |
| Vitamin B additive composition | 19.17 mg |
| Cortisone derivative | 20 mg |

Example Composition 9

| Component | Volume/Amount |
|---|---|
| 0.9 wt.-% sodium chloride solution | 250 mL |
| Diclofenac-sodium | 75 mg |
| Metamizol-sodium | 1.12 g |
| Benzodiazepine | 4 mg |
| Vitamin B additive composition | 19.17 mg |
| Cortisone derivative | 40 mg |

Example Composition 10

| Component | Volume/Amount |
|---|---|
| 0.9 wt.-% sodium chloride solution | 250 mL |
| Diclofenac-sodium | 75 mg |
| Metamizol-sodium | 1.12 g |
| Benzodiazepine | 4 mg |
| Vitamin B additive composition | 19.17 mg |
| Cortisone derivative | 80 mg |

Example Composition 11

| Component | Volume/Amount |
|---|---|
| 0.9 wt.-% sodium chloride solution | 250 mL |
| Diclofenac-sodium | 75 mg |
| Metamizol-sodium | 1.12 g |
| Benzodiazepine | 4 mg |
| Vitamin B additive composition | 19.17 mg |
| Cortisone derivative | 125 mg |

Example Composition 12

| Component | Volume/Amount |
|---|---|
| 0.9 wt.-% sodium chloride solution | 250 mL |
| Diclofenac-sodium | 75 mg |
| Metamizol-sodium | 1.12 g |
| Benzodiazepine | 4 mg |
| Vitamin B additive composition | 19.17 mg |
| Cortisone derivative | 250 mg |

Example Composition 13

| Component | Volume/Amount |
|---|---|
| 0.9 wt.-% sodium chloride solution | 250 mL |
| Diclofenac-sodium | 75 mg |
| Metamizol-sodium | 1.12 g |
| Benzodiazepine | 4 mg |
| Vitamin B additive composition | 19.17 mg |
| Cortisone derivative | 16 mg |

Example Composition 14

| Component | Volume/Amount |
|---|---|
| 0.9 wt.-% sodium chloride solution | 250 mL |
| Diclofenac-sodium | 75 mg |
| Metamizol-sodium | 1.12 g |
| Benzodiazepine | 4 mg |
| Vitamin B additive composition | 19.17 mg |
| Cortisone derivative | 32 mg |

Example Composition 14

| Component | Volume/Amount |
|---|---|
| 0.9 wt.-% sodium chloride solution | 250 mL |
| Diclofenac-sodium | 75 mg |
| Tramadol hydrochloride | 100 mg |
| Diazepam | 4 mg |
| Betamethasone disodium phosphate | 2.6 mg |

Example Composition 15

| Component | Volume/Amount |
|---|---|
| 0.9 wt.-% sodium chloride solution | 250 mL |
| Diclofenac-sodium | 75 mg |
| Tramadol hydrochloride | 100 mg |
| Benzodiazepine | 4 mg |
| Cortisone derivative | 5.3 mg |

Example Composition 16

| Component | Volume/Amount |
|---|---|
| 0.9 wt.-% sodium chloride solution | 250 mL |
| Diclofenac-sodium | 75 mg |
| Tramadol hydrochloride | 100 mg |
| Benzodiazepine | 4 mg |
| Cortisone derivative | 10 mg |

Example Composition 17

| Component | Volume/Amount |
|---|---|
| 0.9 wt.-% sodium chloride solution | 250 mL |
| Diclofenac-sodium | 75 mg |
| Tramadol hydrochloride | 100 mg |
| Benzodiazepine | 4 mg |
| Cortisone derivative | 20 mg |

Example Composition 18

| Component | Volume/Amount |
|---|---|
| 0.9 wt.-% sodium chloride solution | 250 mL |
| Diclofenac-sodium | 75 mg |
| Tramadol hydrochloride | 100 mg |
| Benzodiazepine | 4 mg |
| Cortisone derivative | 40 mg |

Example Composition 19

| Component | Volume/Amount |
|---|---|
| 0.9 wt.-% sodium chloride solution | 250 mL |
| Diclofenac-sodium | 75 mg |
| Tramadol hydrochloride | 100 mg |
| Benzodiazepine | 4 mg |
| Cortisone derivative | 80 mg |

Example Composition 20

| Component | Volume/Amount |
|---|---|
| 0.9 wt.-% sodium chloride solution | 250 mL |
| Diclofenac-sodium | 75 mg |
| Tramadol hydrochloride | 100 mg |
| Benzodiazepine | 4 mg |
| Cortisone derivative | 125 mg |

Example Composition 21

| Component | Volume/Amount |
|---|---|
| 0.9 wt.-% sodium chloride solution | 250 mL |
| Diclofenac-sodium | 75 mg |

-continued

| Component | Volume/Amount |
| --- | --- |
| Tramadol hydrochloride | 100 mg |
| Benzodiazepine | 4 mg |
| Cortisone derivative | 250 mg |

Example Composition 22

| Component | Volume/Amount |
| --- | --- |
| 0.9 wt.-% sodium chloride solution | 250 mL |
| Diclofenac-sodium | 75 mg |
| Tramadol hydrochloride | 100 mg |
| Benzodiazepine | 4 mg |
| Cortisone derivative | 16 mg |

Example Composition 23

| Component | Volume/Amount |
| --- | --- |
| 0.9 wt.-% sodium chloride solution | 250 mL |
| Diclofenac-sodium | 75 mg |
| Tramadol hydrochloride | 100 mg |
| Benzodiazepine | 4 mg |
| Cortisone derivative | 32 mg |

Pain Treatment Studies

For evaluating the pain-alleviating effect of the pharmaceutical composition according to the present invention, medical studies have been performed with human patients, which are summarized in the following.

For each study ten male patients, abbreviated as M1, M2, M3, M4, M5, M6, M7, M8, M9 and M10 for study 1, and abbreviated as M11, M12, M13, M14, M15, M16, M17, M18, M19 and M20 for study 2, were analyzed for each study, respectively.

For each study ten female patients, abbreviated as F1, F2, F3, F4, F5, F6, F7, F8, F9 and F10 for study 1, and abbreviated as F11, F12, F13, F14, F15, F16, F17, F18, F19 and F20 for study 2, were analyzed for each study, respectively.

The male and female patients have been selected randomly.

All patients participating in the studies according to the present invention have experienced severe pain for at least several months, resulting in a visual analog scale (VAS) rating of pain of 8 or more, before any pharmaceutical composition according to the present invention has been administered to the patients in need thereof.

The visual analog scale (VAS) has been determined according to Escalona-Marfil C., et al., Validation of an Electronic Visual Analog Scale mHealth Tool for Acute Pain Assessment: Prospective Cross-Sectional Study, J Med Internet Res. 2020, 22(2), e13468.

To each patient of the respective study, a pharmaceutical composition according to the present invention has been administered until a visual analog scale (VAS) rating of pain of 1 or less than 1 is reached, which means that almost no pain can be observed after administering the pharmaceutical composition according to the present invention.

For each patient the duration of the respective pain treatment study, as well as the visual analog scale (VAS) rating of pain before and after the pain treatment has been recorded.

All patients, which participated in the studies have taken commonly known pain killers during a pre-medication step, without any observable and/or long-lasting effect, resulting in a visual analog scale (VAS) rating of pain of 8 or more. However, to allow for a comparison between the pre-medication step and the administration of the pharmaceutical composition according to the present invention, the type of pain killer, dosage amount of pain killer, duration of treatment and daily time (morning-midday-afternoon-night) of taking the pain killer have been recorded for each patient participating in the studies according to the present invention.

For pain treatment study 1, which is summarized in Table 1 below, the example composition 1 cited above has been applied to all male patients M1 to M10 and to all female patients F1 to F10. Example composition 1 comprises a total volume of 250 ml of 0.9% sodium chloride solution comprising the following components, 75 mg of diclofenac-sodium, 1.12 g of metamizol-sodium, 5 mg of diazepam, and 19.17 mg of Vitamin B additive complex, which in turn comprises 2.7 mg thiamin-hydrochloride, 0.47 mg sodium-riboflavinephosphate, 14 mg nicotinamide, 1 mg dexapanthenol, and 1 mg pyridoxin-hydrochloride.

TABLE 1

| Patient | Pre-medication | Duration of pre-medication | Daily time of pre-medication | VAS pre-medication | Duration of treatment | VAS after treatment |
| --- | --- | --- | --- | --- | --- | --- |
| M1 | 50 mg diclofenac | 6 months | 1-0-1-0 | 9 | 8 days | 1 |
| M2 | 500 mg paracetamol, 400 mg seractil | 8 months | 1-0-1-0 | 8.5 | 5 days | 0.5 |
| M3 | 50 mg diclofenac, 4 mg Xefo | 7 months | 1-0-1-0 | 9.2 | 8 days | 0.8 |
| M4 | 50 mg diclofenac, 400 mg seractil | 12 months | 1-0-1-0 | 9.8 | 10 days | 0.5 |
| M5 | 500 mg paracetamol, 50 mg tramal | 9 months | 1-0-1-0 | 8.2 | 6 days | 0.3 |

TABLE 1-continued

| Patient | Pre-medication | Duration of pre-medication | Daily time of pre-medication | VAS pre-medication | Duration of treatment | VAS after treatment |
|---|---|---|---|---|---|---|
| M6 | 50 mg diclofenac, 400 mg seractil | 6 months | 1-0-1-0 | 9.5 | 9 days | 0.5 |
| M7 | 50 mg tramal, 500 mg proxen | 12 months | 1-0-1-0 | 9.8 | 10 days | 0.8 |
| M8 | 400 mg seractil, 500 mg proxen | 6 months | 1-0-1-0 | 9.8 | 9 days | 0.8 |
| M9 | 400 mg seractil, 500 mg proxen | 12 months | 1-0-1-0 | 8 | 6 days | 0.2 |
| M10 | 50 mg diclofenac, 500 mg paracetamol | 9 months | 1-0-1-0 | 9 | 8 days | 0.8 |
| F1 | 50 mg diclofenac, 500 mg paracetamol | 6 months | 1-0-1-0 | 10 | 10 days | 1.0 |
| F2 | 500 mg proxen, 500 mg novalgin | 2 years | 1-0-1-0 | 9 | 7 days | 0.5 |
| F3 | 50 mg tramal | 10 months | 1-0-1-0 | 8.3 | 6 days | 0.3 |
| F4 | 400 mg seractil, 500 mg proxen | 6 months | 1-0-1-0 | 10 | 9 days | 1.0 |
| F5 | 50 mg diclofenac, 500 mg proxen | 8 months | 1-0-1-0 | 8.2 | 5 days | 0.5 |
| F6 | 50 mg diclofenac, 500 mg paracetamol | 10 months | 1-0-1-0 | 9.2 | 8 days | 0.8 |
| F7 | 50 mg diclofenac, 500 mg paracetamol | 7 months | 1-0-1-0 | 10.0 | 10 days | 1.0 |
| F8 | 50 mg diclofenac, 500 mg paracetamol | 12 months | 1-0-1-0 | 9.5 | 8 days | 1.0 |
| F9 | 50 mg diclofenac, 500 mg novalgin | 8 months | 1-0-1-0 | 9.5 | 9 days | 1.0 |
| F10 | 50 mg diclofenac, 500 mg paracetamol | 6 months | 1-0-1-0 | 8.5 | 5 days | 0 |

For pain treatment study 2, which is summarized in Table 2 below, the example composition 14 cited above has been applied to all male patients M11 to M20 and to all female patients F11 to F20. Example composition 14 comprises a total volume of 250 ml of 0.9% sodium chloride solution comprising the following components, 75 mg of diclofenac-sodium, 100 mg of tramadol-hydrochloride, 5 mg of diazepam, and 2.6 mg betamethasone disodium phosphate.

TABLE 2

| Patient | Pre-medication | Duration of pre-medication | Daily time of pre-medication | VAS pre-medication | Duration of treatment | VAS after treatment |
|---|---|---|---|---|---|---|
| M11 | 100 mg diclofenac, 500 mg proxen | 7 months | 1-0-1-0 | 8.5 | 6 days | 0.5 |

TABLE 2-continued

| Patient | Pre-medication | Duration of pre-medication | Daily time of pre-medication | VAS pre-medication | Duration of treatment | VAS after treatment |
|---|---|---|---|---|---|---|
| M12 | 100 mg diclofenac, 500 mg proxen | 10 months | 1-0-1-0 | 9.2 | 9 days | 0.5 |
| M13 | 500 mg paracetamol | 8 months | 1-0-1-0 | 8.3 | 5 days | 0.5 |
| M14 | 100 mg diclofenac, 500 mg proxen | 12 months | 1-0-1-0 | 8.3 | 7 days | 0.5 |
| M15 | 500 mg paracetamol | 2 years | 1-0-1-0 | 9.0 | 8 days | 0.2 |
| M16 | 100 mg diclofenac, 100 mg tramal | 3 years | 1-0-1-0 | 8.3 | 6 days | 0.5 |
| M17 | 500 mg paracetamol, 100 mg tramal | 5-6 years | 1-0-1-0 | 8.9 | 8 days | 0.9 |
| M18 | 100 mg diclofenac, 500 mg paracetamol | 4 years | 1-0-1-0 | 10.0 | 10 days | 1.0 |
| M19 | 500 mg paracetamol, 100 mg tramal | 9 years | 1-0-1-0 | 9.5 | 9 days | 0.5 |
| M20 | 500 mg paracetamol, 100 mg tramal | 8 years | 1-0-1-0 | 10.0 | 10 days | 0.8 |
| F11 | 100 mg diclofenac, 500 mg paracetamol | 6 months | 1-0-1-0 | 9.0 | 7 days | 0.5 |
| F12 | 100 mg diclofenac (retard) | 7 months | 1-0-1-0 | 10 | 10 days | 1.0 |
| F13 | 100 mg diclofenac (retard) | 8 months | 1-0-1-0 | 8.5 | 6 days | 0.8 |
| F14 | 100 mg diclofenac (retard) | 12 months | 1-0-1-0 | 8.3 | 5 days | 0 |
| F15 | 100 mg diclofenac (retard), 500 mg paracetamol | 8 months | 1-0-1-0 | 8.8 | 8 days | 0.8 |
| F16 | 500 mg paracetamol, 500 mg novalgin | 1 year | 1-0-1-0 | 9.2 | 8 days | 1.0 |
| F17 | 100 mg diclofenac (retard), 500 mg proxen | 8 months | 1-0-1-0 | 8.7 | 5 days | 0.5 |
| F18 | 100 mg diclofenac (retard), 500 mg paracetamol | 6 years | 1-0-1-0 | 9.8 | 10 days | 0.8 |
| F19 | 100 mg diclofenac (retard), 500 mg paracetamol | 9 months | 1-0-1-0 | 8.3 | 6 days | 0.4 |
| F20 | 100 mg diclofenac (retard), 400 mg seractil | 7 months | 1-0-1-0 | 9.0 | 8 days | 0.6 |

From both table 1 and 2 the effectiveness of the pharmaceutical compositions of the present invention, in particular the effectiveness of example compositions 1 and 14 when compared to conventional pain treatments can be derived.

As can be derived from tables 1 and 2 all of the patients participating in the pain treatment studies have suffered from very severe pain for months and sometimes even years, with a VAS rating of pain of at least 8, without any significant effect of the conventional pain treatments according to the premedication step.

By contrast, when applying the example composition 1 and 14 according to the present invention, a significant improvement in the VAS rating of pain of all patients can be observed within a couple of days, resulting in a VAS rating of pain of less than 2 or sometimes even 1 or less.

While the superior effect of the pharmaceutical compositions of the present invention have been demonstrated in table 1 and 2 in detail only for example composition 1 and 14, a superior pain relieving effect in human patients can be demonstrated for all example compositions 1 to 23 in particular and in general also for all pharmaceutical compositions of the present invention. In particular the pharmaceutical compositions of the present invention encompassed by the embodiments and preferred selections according to the generic disclosure result in a significant decrease of the VAS rating of pain within a short period of time, which can be observed in a huge variety of different patients.

Although specific advantages have been enumerated above, various embodiments may include some, none, or all of the enumerated advantages. Other technical advantages may become readily apparent to one of ordinary skill in the art after review of the following figures and description. It is understood that, although exemplary embodiments are illustrated in the figures and described below, the principles of the present disclosure may be implemented using any number of techniques, whether currently known or not. Modifications, additions, or omissions may be made to the systems, apparatuses, and methods described herein without departing from the scope of the invention. The components of the systems and apparatuses may be integrated or separated. The operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set. It is intended that the claims and claim elements recited below do not invoke 35 U.S.C. § 112(f) unless the words "means for" or "step for" are explicitly used in the particular claim. The above-described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:

1. A pharmaceutical composition, wherein the pharmaceutical composition is an injectable or infusible pharmaceutical composition, comprising:
   a) a pharmaceutically acceptable solvent,
   b) a first active compound being an oxicam selected from lornoxicam or a pharmaceutically acceptable salt or solvate thereof,
   c) a second active compound comprising metamizole or tramadol or a pharmaceutically acceptable salt or solvate thereof, and
   d) a third active compound comprising at least one benzodiazepine or a pharmaceutically acceptable salt or solvate thereof,
   wherein the pharmaceutical composition further comprises dexamethasone sodium, betamethasone sodium, methylprednisolone sodium, prednisolone sodium, or triamcinolone acetonide potassium.

2. The pharmaceutical composition according to claim 1, wherein the at least one benzodiazepine or pharmaceutically acceptable salt or solvate thereof comprises at least one of diazepam, chlonazepam or a pharmaceutically acceptable salt or solvate thereof.

3. The pharmaceutical composition according to claim 1, wherein the third active compound comprises from 0.00001 wt. % to 0.00004 wt. % of the least one benzodiazepine or pharmaceutically acceptable salt or solvate thereof.

4. The pharmaceutical composition according to claim 1, wherein the the first active compound is selected from 0.000008 wt. % to 0.000128 wt. %, from 0.000032 wt. % to 0.000096 wt. %, or 0.000032 wt. % or 0.000064 wt. % of lornoxicam or a pharmaceutically acceptable salt or solvate thereof.

5. The pharmaceutical composition according to claim 1, wherein the pharmaceutical composition further comprising paracetamol or a pharmaceutically acceptable salt or solvate thereof.

6. The pharmaceutical composition according to claim 1, wherein the second active compound comprises from 0.002 wt. % to 0.01 wt. % of metamizole or a pharmaceutically acceptable salt or solvate thereof.

7. The pharmaceutical composition according to claim 1, wherein the second active compound comprises from 0.0002 wt. % to 0.0008 wt. %, from 0.0003 wt. % to 0.0006 wt. %, or 0.0004 wt. % of tramadol or a pharmaceutically acceptable salt or solvate thereof.

8. The pharmaceutical composition according to claim 1, further comprising a vitamin B additive composition, wherein the vitamin B additive composition comprises thiamine, riboflavin, nicotinamide, cobalamin, dexapanthenol and/or pyridoxin or a pharmaceutically acceptable salt or solvate thereof.

9. The pharmaceutical composition according to claim 1, wherein the pharmaceutically acceptable solvent is selected to form an aqueous solution comprising sodium chloride, calcium chloride, potassium chloride, magnesium chloride, sodium acetate and/or glucose.

10. The pharmaceutical composition according to claim 3, wherein the third active compound comprises from 0.000016 wt. % to 0.00003 wt. % of the least one benzodiazepine or pharmaceutically acceptable salt or solvate thereof.

11. The pharmaceutical composition according to claim 10, wherein the third active compound comprises from 0.000016 wt. % to 0.000025 wt. % of the least one benzodiazepine or pharmaceutically acceptable salt or solvate thereof.

12. The pharmaceutical composition according to claim 11, wherein the third active compound comprises 0.00002 wt. % of the least one benzodiazepine or pharmaceutically acceptable salt or solvate thereof.

13. The pharmaceutical composition according to claim 5, wherein the paracetamol comprises from 0.001 wt. % to 0.008 wt. % of paracetamol or a pharmaceutically acceptable salt or solvate thereof.

14. The pharmaceutical composition according to claim 13, wherein the paracetamol comprises from 0.0025 wt. % to 0.008 wt. % of paracetamol or a pharmaceutically acceptable salt or solvate thereof.

15. The pharmaceutical composition according to claim 14, wherein the paracetamol comprises from 0.004 wt. % or 0.008 wt. % of paracetamol or a pharmaceutically acceptable salt or solvate thereof.

16. The pharmaceutical composition according to claim 6, wherein the second active compound comprises from 0.003 wt. % to 0.007 wt. % of metamizole or a pharmaceutically acceptable salt or solvate thereof.

17. The pharmaceutical composition according to claim 16, wherein the second active compound comprises from 0.003 wt. % to 0.005 wt. % of metamizole or a pharmaceutically acceptable salt or solvate thereof.

18. The pharmaceutical composition according to claim 17, wherein the second active compound comprises 0.005 wt. % of metamizole or a pharmaceutically acceptable salt or solvate thereof.

* * * * *